United States Patent [19]

Laine et al.

[11] Patent Number: 5,352,607
[45] Date of Patent: Oct. 4, 1994

[54] MOLECULAR CLONE OF A CHITINASE GENE FROM VIBRIO PARAHEMOLYTICUS

[75] Inventors: Roger A. Laine, Baton Rouge, La.; Chin-Yih Ou, Dunwoody, Ga.; Jesse M. Jaynes, Baton Rouge, La.

[73] Assignee: Louisiana State University and Agricultural College, Baton Rouge, La.

[21] Appl. No.: 876,894

[22] Filed: Apr. 29, 1992

Related U.S. Application Data

[63] Continuation of Ser. No. 620,909, Dec. 3, 1990, abandoned, which is a continuation of Ser. No. 53,029, May 22, 1987, abandoned.

[51] Int. Cl.$^5$ .................. C12N 1/21; C12N 15/31; C12N 15/52; C12N 15/70
[52] U.S. Cl. .................. 435/252.33; 435/172.3; 435/220; 435/320.1; 435/909; 536/23.2; 536/23.7
[58] Field of Search ............... 435/69.1, 172.3, 252.33, 435/220, 320.1, 909; 536/23.2, 23.7; 975/6, 22, 59, 60, 66, 72, 73

[56] References Cited

U.S. PATENT DOCUMENTS 4,751,081  6/1988  Suslow et al. .................. 424/93

OTHER PUBLICATIONS

Soto-Gil et al., 1985, *Chemical Abstracts*, vol. 102, Abstract No. 21624g, p. 180.
Ohtakara et al., 1979, Chemical Abstracts, vol. 91, Abstract No. 86189g, p. 320.

*Primary Examiner*—Richard A. Schwartz
*Assistant Examiner*—J. LeGuyader
*Attorney, Agent, or Firm*—William David Kiesel; Robert C. Tucker; Warner J. Delaune, Jr.

[57] ABSTRACT

A process for cloning the chitinase gene of *Vibrio parahemolyticus* is provided, comprising the steps of cleaving the *Vibrio parahemolyticus* DNA with Sau3A, PSTI or other restriction enzyme, mixing the cleaved DNA fragments in the presence of pUC18 and T4 ligase to produce a composite plasmid, and inserting the composite plasmid in a DH5a strain of *E. Coli*.

8 Claims, 3 Drawing Sheets

MOLECULAR CLONE OF A CHITINASE GENE FROM VIBRIO PARAHEMOLYTICUS

This invention was made with government support under grant NA81AA-D-00103 awarded by the National Oceanic and Atmospheric Administration, United States Department of Commerce. The government has certain rights in this invention.

This is a continuation of abandoned application Ser. No. 07/620,909 filed on Dec. 3, 1990 which is a continuation of abandoned application Ser. No. 07/053,029 filed on May 22, 1987.

BACKGROUND OF THE INVENTION

1. Field of the Invention

This invention relates in general to a method of producing a cloned chitinase enzyme, as well as to a cloned chitinase enzyme from *Vibrio parahemolyticus*.

2. Prior Art

Chitin is a polymer of beta 1-4 linked 2-dexoy-2-acetamidoglucopyranose (poly-N-acteylglucosamine) which is one of the largest sources of renewable biomass on earth, second only to cellulose and lignins. For example, chitin forms the exo-skeleton of insects and crustaceans and is a component of cell walls in some fungi and yeasts.

The first and most important step in the natural breakdown of this substance occurs when microbes and fungi secrete the enzyme chitinase which degrades the largely insoluble polymer to di-N-acteyl chitobiose. A usual second step involves the enzyme chitobiase which degrades the soluble chitobiose to N-acteylglucosamine. This substance, since it contains bound nitrogen and, as a sugar, is a carbon source, could be utilized for many fermentation processes such as a valuable feed stock for obtaining single cell protein, or as a feed supplement for pisci-culture, chickens, pigs or cattle.

Sources of chitin that are now principally considered a waste by-product would include shellfish shells. More particularly, crayfish, shrimp and crab shells, which consists mainly of chitin, protein and calcium carbonate would make excel lent sources or chitin, since approximately 25-58% of the shellfish waste is chitin.

Unfortunately, the industrial use of the degradation products chitobiose and N-acetyl glucosamine have been restricted by the expense and unavailability of these substances. Much of the research performed thus far on commercial use of chitin in shellfish waste has taken place since 1957. L. R. Berger studied digestion of chitin by an enzyme called chitinase from a streptomyces species. "Digestion of chitin by a Streptomyces Species", L. R. Berger, Ph.D. Thesis, University of California, Davis, Calif. In 1970 J. G. Chan studied chitin degrading organisms in Puget Sound and reported his findings in "The Occurrence, Taxonomy, and Activity of Chitinoclastic Bacteria from Sediment, Water, and Fauna of Puget Sound", J. G. Chart, Ph.D. Thesis, University of Washington, Seattle, Wash. The United States Environmental Protection Agency in 1971 noted concerns about pollution caused by shellfish waste. "Pollution Abatement and By-product Recovery in Shellfish and Fisheries Processing", Project # 12130FJQ, Environmental Protection Agency, Washington, D.C. In 1975, B. L. Averback investigated the structure of chitin and chitosan. "The Structure of Chitin and Chitosan, M.I.T. Sea Grant Program Report # MITSG77E, Index #77-703Z1e, Massachusetts Institute of Technology, Cambridge, Mass. Then, in 1977, N. A. Ashford, et al. reported on industrial prospects for chitin and protein recovery from shellfish waste. "Industrial Prospects for Chitin and Protein from Shellfish Wastes", M.I.T. Sea Grant Program #MITSG-77-3, Index #77-703-Z1e, Massachusetts Institute of Technology, Cambridge, Mass. A year later, P. A. Carroad and R. A. Tom proposed a process conception and selection of microorganisms for bioconversion of shellfish chitin wastes. "Bioconversion of Shellfish Chitin Wastes: Process Conception and Selection of Microorganisms, *Journal of Food Science*, Vol. 43, pages 1158-1161. They singled out a *Serratia marcescens* and a *Bacillus cereus* as the most promising chitinase enzyme producers for exploitation. D. M. Ogrydziak and J. D. Reid, in 1980, described an isolate of *Serratia marcescens* as a mutant overproducer of the enzyme chitinase. "Chitinase-Overproducing Mutant of *Serratia Marcescens*" *Applied & Environmental Microbiology*, Vol. 41, page 664. In 1981, R. A. Tom and P. A. Carroad reported on the effects of reaction conditions on hydrolysis of chitin by the enzyme from Ogrydziak's mutant *Serratia marcescens*. "Effect of Reaction Conditions on Hydrolysis of Chitin by *Serratia marcescens* QMB 1466 Chitinase," *Journal of Food Science* 46, pages 646–647. I. G. Casio et al. proposed in 1982 a scheme for bioconversion of chitin from shrimp shell waste with several acid and base pretreatments, followed by chitinase from *Serratia marcescens*. "Bioconversion of Shellfish Chitin Waste: Waste Pretreatment, Enzyme Production, Process Design, and Economic Analysis," *Journal of Food Science* 47, pages 901-905. They suggested a process design and performed an economic analysis that indicated a negative after-tax cash flow of $0.06/kg. However, several of the expensive factors in the economic analysis of biodegradative processing of shrimp shell waste used in performing the economic analysis could be mitigated by today's technology. In 1986, two chitinase genes from *Serratia marcescens* QMB1466, have been reported by R. L. Fuchs, S. A. McPherson and D. J. Drahos in "Cloning of a *Serratia marcescens* Gene Encoding Chitinase", *Applied Environmental Microbiology* 51, 504–509 and by J. D. G. Jones, K. L. Grady, T. V. Suslow and J. R. Bedbrook in "Isolation and Characterization of Genes Encoding Two Chitinase Enzymes from *Serratia marcescens*", *EMBO* 5, 467–473, to have been cloned in *E. coli* and the nucleotide sequence of one of these genes determined.

However, the physical stability of the chitinase from *Serratia marcescens* is not as great as would be desired. Furthermore, accessibility of the substrate, chitin, by the enzyme is limited by the presence of proteins and calcium carbonate, which are, by current technology, removed by treatment with a base, and an acid, respectively. A chitinase enzyme to be used in the latter system would be much better if it is salt-tolerant, since, after neutralization of the acid or base treatment, perhaps 1M salt would be present. A process step for removal of the salt prior to digestion is a time-consuming and expensive step. For this reason the more stable chitinase enzyme from *Vibrio parahemolyticus*, a halophilic microorganism which requires 2-7% sodium chloride for growth, could possibly serve as a better enzyme for digestion of chitin from shellfish, than those from *Serratia marcescens* and *Streptomyces griseus*. Chitinases isolated from an unidentified species of Vibrio have been reported in 1979 by Y. Uchida, M. Misutome and A. Ohitakara in "Isolation of a Chitinase EC- 3.2.1.14 Producing Bacterium: Culture Conditions for Enzyme Production and Properties of the Enzymes," *Japan Fermentation Technology* 57, 131–140, as well as in "Purification and Some Properties of Chitinase EC-3.2.1.14 from Vibrio Species," *Japan Fermentation Technology* 57, 169–177.

SUMMARY OF THE INVENTION

Therefore, it is an object of this invention to determine if a chitinase enzyme from *Vibrio parahemolyticus* would digest chitin from shellfish.

Another object of this invention is to determine if a process for cloning a chitinase gene of *Vibrio parahemolyticus* having the characteristics of digesting chitin from shellfish is possible.

Still another object of this invention is to produce a *Vibrio parahemolyticus* chitinase gene clone.

A further object of this invention is to produce an *E. coli* clone, expressing, and secreting chitinase from *Vibrio parahemolyticus*.

Other objects and advantages of this invention shall become apparent from the ensuing descriptions of the invention.

Accordingly, a process for cloning a chitinase gene of *Vibrio parahemolyticus* is disclosed, comprising (a) cleaving *Vibrio parahemolyticus* DNA with a Sau3A or other restriction enzyme such as PSTI, then (b) mixing DNA of 5–8 kbp with restriction enzyme-cleaved pUC18 or other plasmid vector and T4 ligase to produce a composite plasmid, and then (c) inserting the composite plasmid into *E. coli* or other bacteria, plants or yeast.

PREFERRED EMBODIMENTS OF THE INVENTION

Figure 1:
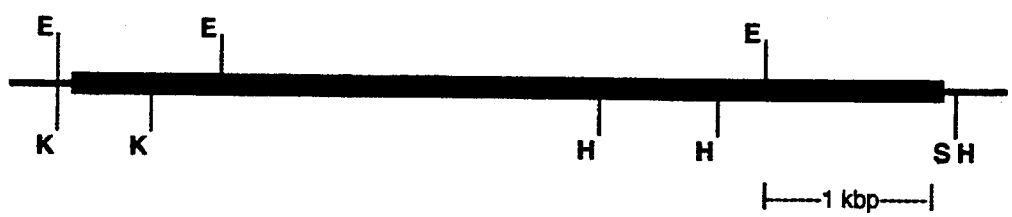
FIG. 1 is a restriction endonuclease map of pC139 carrying a chitinase gene shown as thick closed bars wherein the abbreviations for the endonuclease sensitive sites are E: EcoR-1, H: Hind-III, K: Kpn-I and S: Sal-I.

The *Vibrio parahemolyticus* (ATCC 27969) enzyme was propagated in an enriched 804 medium (0.75 gm/a KCl, 6.9 gm/a MgSO4 7H2O, 23.4 gm/1 NaCl, 1 gm/1 tryptone and 1 gm/1 yeast extracts). The *E. coli* strains, DH5a, used as described below, as the bacterial host for recombinant plasmids were grown in an LB (Luria-Bertani) medium and was supplemented with ampicillin (50 ug/ml).

Restriction endonucleases, T4 ligase, in vitro package reagents and competent DH5a cells used in the tests described herein were all purchased from Bethesda Research Laboratories; chitin and chitosan, chitobiose, and p-nitrophenyl N-acetyl glucosaminide were purchased from Sigma; alpha dCTP was purchased from ICN Biochemicals, Inc.; and tritium labeled acetic anhydride was purchased from Amersham. Swollen chitin was prepared from crab chitin (Sigma, practical grade) with a treatment of phosphoric acid according to the process described by J. Monreal and E. T. Reese in "The Chitinase of *Serratia marcescens*", *Canadian Journal Microbiology*, Vol. 14, pages 689–696. Chitin agar plates used for selecting chitinase-producing *E. coli* contain 1.5% Bactoagar, 0.25 (w/v) swollen chitin, 1% each of Bacto tryptone and yeast extract, 10 gm/1 NaCl and 50 ug/ml ampicillin. Regenerated and tritium labeled chitin were prepared by acetylation of chitosan as described by S. Hirano et al. in "Selective N-acetylation of Chitin," Carbohyd. Res. 47: 315–320 and J. Molano et al. in "A Rapid and Sensitive Assay for Chitinase Using Tritiated Chitin," Anal. Biochem. 83: 648–656 respectively.

Both phage and plasmid DNA libraries of the chromosomal DNA of *Vibrio parahemolyticus* were constructed. The chromosomal DNA was partially digested with Sau3A restriction endonuclease and fractionated in a 10–40% sucrose gradient. DNA of 5–8 kbp and 7–12 kbp were introduced into the BamH-I sites of pUC18 plasmid and Charon 28 phage DNA, respectively. Recombinant pUC18 DNA was used to transform competent *E. coli* DH5a cells. Recombinant Charon 28 DNA was in vitro packages and was used to infect LE329 cells. Five hundred and ten individual bacterial colonies with Vibrio-pUC18 DNA were stabbed into chitin-LB plates and were incubated at 37° C. for 24 hours and then at 23° C. for two weeks. A chitin-digested halo zone developed around one of these colonies in nine days. Plasmid DNA was prepared from this clone (pC139) and used to transform DH5a cells again. All the resultant transformants were able to produce and secure chitinase and create halo zones in chitin plates.

Chromosomal DNA of *Vibrio parahemolyticus* was digested with restriction endonucleases according to manufacturer's recommendations. DNA was electrophoresed in an agarose gel and transferred onto a nitrocellulose filter, hybridized with a nick-translated DNA probe as described previously by C. Y. Ou et al. in "A novel sequence segment and other nucleotide structural features in the long terminal repeat of a BALB/c mouse genomic leukemia virus-related DNA clone. *Nucleic Acid Research*. 11: 5603–5620. Nick-translated pC139 DNA was prepared according to P. Rigby et al. in "Labeling deoxynucleic acids to high specific activity in vitro by nick-translation with DNA polymerase", *I. J. Mol. Biol.* 113:237–251, and had a specific activity of $2 \times 10$ cpm/ug. To demonstrate that the pC139 plasmid carries a chitinase gene, in batch of five hundred milliliters of *E. coli* carrying pC139 or pUC18 plasmid was grown in medium supplemented with 0.5% (w/v) swollen chitin for 36–48 hours. The media were centrifuged at $4,000 \times g$ for 10 minutes and the supernatant containing the extra-cellular chitinase was concentrated 10-fold with an Amicon pressure cell equipped with a pM10 filter (cutoff=10,000 da) followed by an extensive dialysis against 50 mM potassium phosphate (KP) buffer, pH 6.0. The cell pellet was washed once with 20 ml of SET buffer (15% sucrose, 50 mM Tris HCl pH 7.5, 10 mM EDTA) and centrifuged at the same rate again. Washed cells were then resuspended in 20 ml SET buffer containing 20 mg lysozyme, cooled on ice for 10 minutes, followed by an additional of 20 ml of Triton X-100 solution (10% Triton X-100, 50 mM Tris Hcl, pH 7.5, 10 mM EDTA). These total cell extracts were centrifuged at $25,000 \times g$ for 60 minutes to remove chromosomal DNA and were dialyzed against KP buffer. The presence of lysozyme in the enzyme preparation did not interfere with the detection of chitinase.

Fifty ml of concentrated extra-cellular medium (equivalent to 500 ml original culture) and 10 ml intracellular extract (equivalent to 50 ml or original culture) were loaded onto DEAE BioGel A columns (10 ml bed volume) equilibrated with KP. Columns were eluted with potassium phosphate buffers containing 0.1M and 0.3M NaCl. Chitinase was eluted in 0.3M NaCl fractions and was further concentrated with an Amicon pressure cell equipped with a PM 10 filter. One ml of these concentrated extra- and intra-cellular chitinase preparations are equivalent to 333 ml and 8 ml, respectively, of original culture. *Vibrio parahemolyticus* was grown in an 804 medium, supplemented with 0.5% (w/v) swollen chitin. The production of chitinase was judged by the disappearance of chitin chips in the medium. After the complete disappearance of chitin (usually 36–48 hours at 37° C.), the medium was collected, concentrated with an Amicon pressure cell equipped with a PM10 filter and dialyzed extensively against KP buffer. Dialyzed chitinase solution was applied onto a DEAE-BioGel A column, and eluted with KP containing 0.1M NaCl followed by 0.3 NaCl. Chitinase was eluted in the 0.3M fractions. These chitinase-containing fractions were pooled and mixed with an equal volume of complete adjuvant and were used to immunize three rabbits. The rabbits received four subcutaneous injections with intervals of 3 weeks, and were then bled with the anti-chitinase titer reached 1:16 as judged by Ouchterlony double diffusion. The plasmid DNA, designated pC139, from this *E. coli* was isolated and shown to have 5.9 kbp Vibrio DNA insert. A restriction enzyme map was constructed and shown in FIG. 1. Nick-translated pC139 DNA hybridized with a 3.7 kbp EcoR-I fragment and a 0.7 kbp. Hind-III DNA fragments (FIG. 2) which was predicted by the restriction map of pC139. Since the chromosomal Vibrio DNA used for the construction of the plasmid library was partially digested with Sau3A enzyme, it was possible that some of the insert segments in the pC139 were derived from different locations in the Vibrio chromosome and were joined together in the ligation step of the initial cloning procedure. It is clear, however, that the 3.7 kbp internal EcoR-I segment was not generated from such an event. There are only two other EcoR-I fragments, and two other Hind-III fragments (larger that 9 kbp, and 3.2 kbp) which appear to be the sequences flanking the 3.7 kbp EcoR-I and 0.7 kbp Hind-III internal segments, respectively. There is only one segment each for BamH-I, Sal-I and Bgl-II fragments detected by the pC139 probe. These results strongly suggested that most, if not all, of the 5.0 kbp insert DNA was derived from one continuous segment from the chromosomal DNA.

Figure 3:
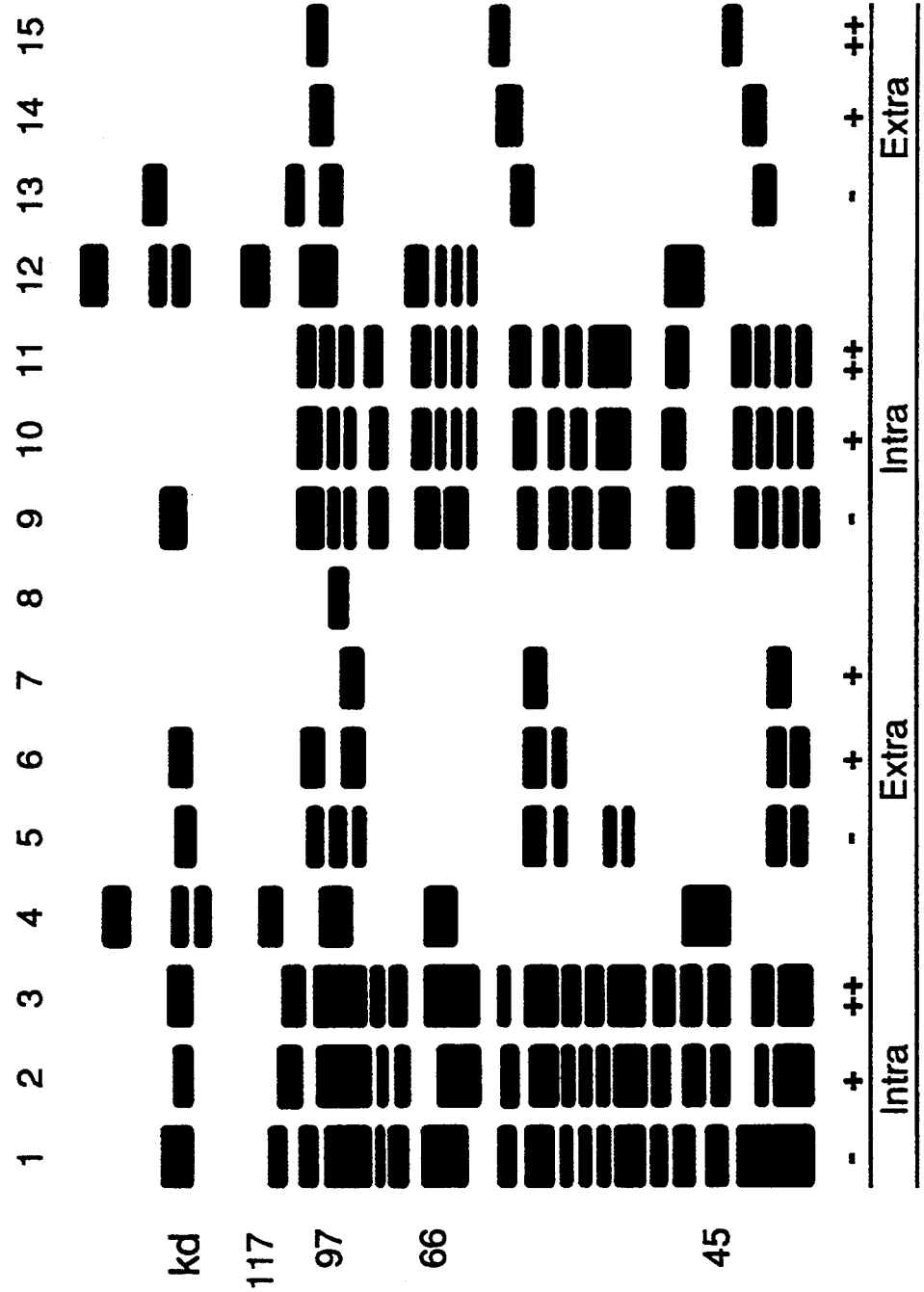
FIG. 3 illustrates the results of a SDS-gel electrophoresis analysis of the cloned chitinase isolated from cell culture extract of pC139-carrying DH5a strain of *E. coli*.

Nitrophenyl b-N acetyl glucosaminide, an analogue of chitobiose, can be cleaved by either chitobiase or b-N-acetyl hexosaminidases to produce the yellow dye nitrophenol. With this substrate, we cannot detect any chitobiase or b-N-hexosaminidase activity in pC139 clone, thus it appears that the pC139 clone does not encode a functional chitobiase. It has been reported by M. Nishibuchi and J. Kaper in "Nucleotide sequence of the thermostable direct hemolysin gene of *Vibrio parahemolyticus*," *J. Bacteriol.* 162: 5580564, that, although hemolysin was produced by *E. coli* carrying the cloned hemolysin gene from *Vibrio parahemolyticus*, extracellular secretion of hemolysin was undetectable. A. T. Wortman et al. in "Chitinase determinants of *Vibrio vulnificus*: Gene cloning and applications of chitinase probe" *Appl. and Environ. Microbiol.* 52: 142–145, were unable to detect any chitinolytic activity in the extra-cellular medium in their *E coli* clone carrying a chitinase determinant of *Vibrio vulnificus*. In order to evaluate the efficiency of chitinase secretion in *E. coli*, the extracellular and intro-cellular pools of cloned chitinases were examined. The *E. coli* carrying pC139 were grown overnight in LB containing 50 ug/ml of ampicillin. Extracellular medium and cell extract were isolated and applied onto a DEAE-BioGel A column. Chitinase activities were found to be present in the 0.3 NaCl fractions. These chitinase-containing fractions were examined by SDS-gel electrophoresis and the results are shown in FIG. 3. As compared to the corresponding fractions from *E. coli* carrying pUC18 plasmid (lanes 9 and 13), there was an additional 95 kd peptide in the intracellular (lane 1) and extracellular (lane 5) preparations isolated from the pC139-carrying *E. coli*. The apparent molecular weight (95 kd) of this additional peptide is indistinguishable from the purified chitinase of *Vibrio parahemolyticus* (lane 8). This 95 kd peptide can be selectively removed from the enzyme preparation by affinity-adsorption with particulate chitin as described by R. L. Roberts and E. Cabib in "*Serratia marcescens* chitinase: One step purification and use for the determination of chitin" Anal. Biochem. 127:404–412. Removal of the 95 kd peptide was proportional to the amount of chitin added (compare lanes 2–4 and lanes 5–7). It is clear that while only 70% of the 95 kd peptide was removed as shown in lane 6, most, if net all, of it was removed when the added chitin was increased two-fold as shown in lane 7. The supernatants (lanes 3 and 7) after chitin adsorption lost their chitinolytic activity as measured by their inability to degrade tritium labeled chitin and to generate yellow colored nitrophenol from nitrophenyl N, N' diacetyl chitobiose (an analogue of chitotriose). This removal of 95 kd chitinase peptide by chitin-adsorption appeared to be highly specific; no apparent change in other peptide bands were observed in preparations of pC139 and pUC18 carrying cells.

In addition to the SDS-PAGE and the chitin adsorption test described above, we also examined the antigenicity of the clone chitinase enzyme with the rabbit antiserum against the Vibrio chitinase. The rabbit anti-chitinase serum formed a precipitin line of identity with the chitinases isolated from Vibrio and from *E. coli* carrying the pC139 plasmid. Cell extract isolated from *E. coli* carrying a pUC18 plasmid did not react with the antiserum. This result clearly showed that the cloned chitinase enzyme shared an antigenic determinant(s) with the Vibrio chitinase.

The chitinase gene of *Vibrio parahemolyticus* has been isolated from a pUC19 plasmid library. This *E. coli* clone (pUC18) produced sufficient amounts of chitinase to hydrolyze chitin in the agar medium and form a clear halo surrounding the bacterial colony.

The Vibrio insert DNA is 5.9 kbp in length and apparently contains the entire chitinase gene. No chitobiase or b-N acetyl hexosaminidase activity was detected in the pC139 clone. However, whether a truncated chitobiase gene is included in the pC139 clone remains to be determined. The cloned enzyme (FIG. 3, lanes 2 and 5) has an apparent molecular weight of 95 kd which is indistinguishable from its parental enzyme (lane 8) and is readily adsorbed by chitin. The expression of the cloned gene is not affected by the addition of IPTG (isopropyl thiogalactose) in the culture medium (data not shown) and appears to be regulated by a Vibrio promoter which functions in the *E. coli* host. A few genes from the genus Vibrio have been cloned in *E. coli*. Cholera enterotoxin is normally secreted by *Vibrio cholerae*, but not by *E. coli* containing a cloned cholera toxin gene (17). Hemolysin was detected in cell lysates of HB101 containing cloned hemolysin gene of *Vibrio parahemolyticus*, no zones of hemolysis were observed when this clone was grown on a blood agar plate. This report strengthened the probability that the chitinase enzyme from pC139 was secreted and not due to bacteriolysis. Recently, Worthman et al. were unable to detect any extracellular chitinolytic in their *E. coli* clones carrying the chitinase gene of *Vibrio vulnificus*. These authors isolated a clone Vibrio DNA containing a chitobiase gene and subsequently found the juxtaposited chitinase gene. Thus, it appears to be a general rule that the promoters of Vibrio spp. did not function well in *E. coli*. Our pC139 clone, however, both expresses and secretes chitinase into the medium.

During the process of molecular cloning of the chitinase gene of *Vibrio parahemolyticus*, we also isolated a b-D-hexosaminidase gene, designated pC120.

Chitinase is an anti-fungal agent. We are employing this chitinase for studies of anti-fungal activities in food, medical, and research products. We are cloning the gene into plants, bacteria and animal cells as an anti-fungal agent.

A deposit of aDH5a strain of *E. coli* carrying the pC139 plasmid has been deposited with the Department of Agriculture, Agricultural Research Service, 1815 North University St., Peoria, Ill. 61604, and assigned deposit number NRRL B-18200. The deposit was received and accepted by the Agricultural Research Service on Apr. 9, 1987 and May 12, 1987 respectively. Deposit was made according to the Budapest Treaty on the International Recognition of the Deposit of Microorganisms For the Purposes of Patent Procedure.

There are, of course, many obvious alternate embodiments and modifications of this invention which are intended to be included within the scope of this invention as defined by the following claims.

What I claim is:

1. A composite DNA molecule comprising:
   (a) a fragment of cleaved *Vibrio parahemolyticus* DNA from pC139 containing a chitinase gene which expresses a chitinase of approximately 95 Kd or a fragment of said gene which produces an active chitinase; and
   (b) a vector ligated to said fragment wherein said vector is a plasmid or phage.

Figure 2:
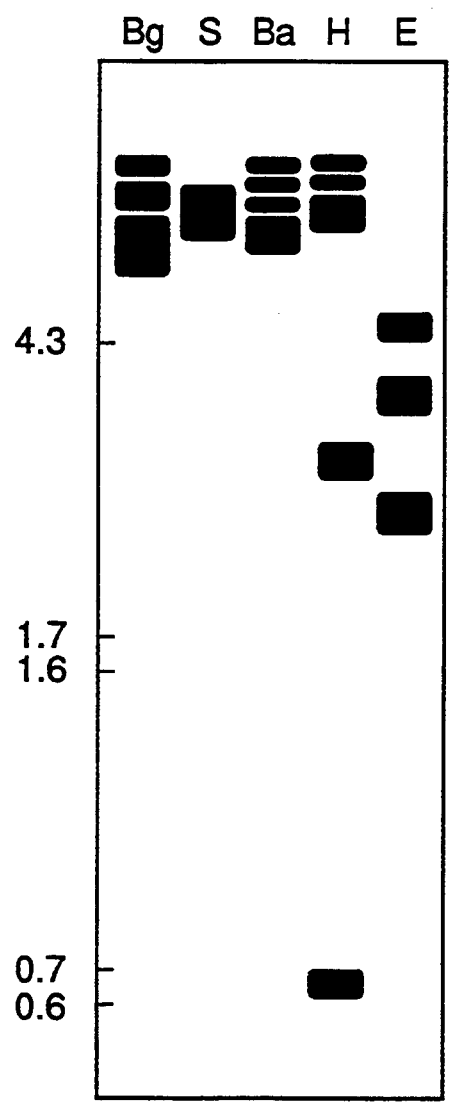
FIG. 2 is a SDS-polyacrylamide gel electrophoretic analysis of cloned chitinase isolated from cell extract of pC139-carrying DH5a strain of *E. coli*.

2. A composite DNA molecule according to claim 1, wherein said fragment has restriction endonuclease digestion sites as shown in FIG. 1.

3. A composite DNA molecule according to claim 2, wherein said *Vibrio parahemolyticus* DNA is cleaved with Sau3A.

4. A composite DNA molecule according to claim 1 wherein said vector is cleaved with BamHI prior to ligating to said fragment.

5. A composite DNA molecule according to claim 4 wherein said vector is pUC18.

6. An *E. coli* microorganism carrying a recombinant plasmid pC139.

7. A strain of *E. coli* identified as NRRLB-18200.

8. A composite DNA molecule containing a *Vibrio parahemolyticus* chitinase gene comprising:
   (a) a fragment of cleaved *Vibrio parahemolyticus* DNA from pC139 containing a chitinase gene which expresses a chitinase of approximately 95 Kd; and
   (b) a vector ligated to said fragment at the BamH-I site, wherein said vector is a plasmid or phage.

* * * * *